US00PP36116P2

(12) United States Plant Patent
Chaussard

(10) Patent No.: US PP36,116 P2
(45) Date of Patent: Sep. 17, 2024

(54) ***DASIPHORA* PLANT NAMED 'MINPOROUG01'**

(50) Latin Name: *Dasiphora fruticosa*
Varietal Denomination: MINPOROUG01

(71) Applicant: Hortival Diffusion SAS, Beaufort en Anjou (FR)

(72) Inventor: Pierre Chaussard, Saint Mathurin sur Loire (FR)

(73) Assignee: Hortival Diffusion SAS (FR)

( * ) Notice: Subject to any disclaimer, the term of this patent is extended or adjusted under 35 U.S.C. 154(b) by 0 days.

(21) Appl. No.: 18/540,238

(22) Filed: Dec. 14, 2023

(51) Int. Cl.
*A01H 5/02* (2018.01)
*A01H 6/74* (2018.01)

(52) U.S. Cl.
USPC ..... Plt./237

(58) Field of Classification Search
USPC ..... Plt./237
See application file for complete search history.

*Primary Examiner* — Susan McCormick Ewoldt
(74) *Attorney, Agent, or Firm* — Cassandra Bright

(57) ABSTRACT

A new and distinct cultivar of *Dasiphora* plant named 'MINPOROUG01' is disclosed, characterized by fade-resistant, reddish-orange flowers with a pinkish-orange tint. The new variety is a *Dasiphora*, normally produced as an outdoor garden or container plant.

2 Drawing Sheets

Figure 1:
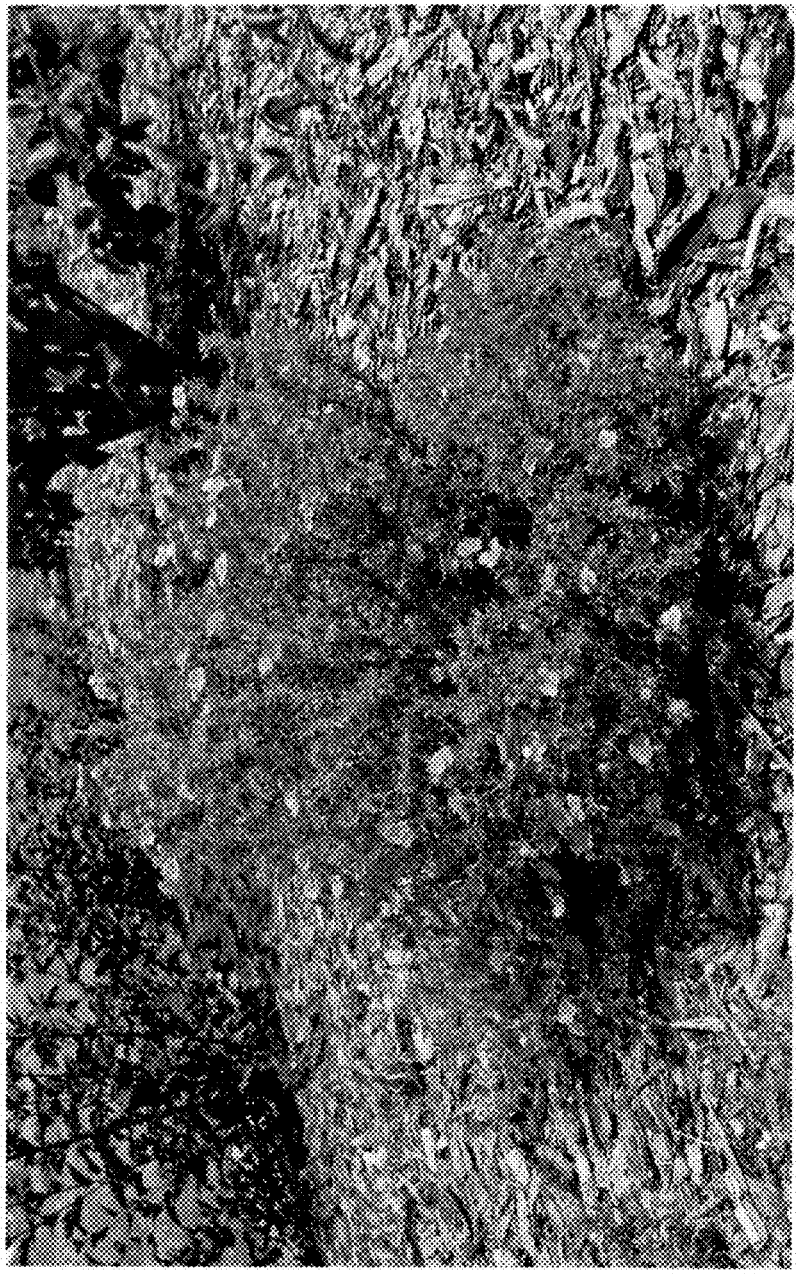

Latin name of the genus and species: *Dasiphora fruticosa*.
Variety denomination: 'MINPOROUG01'.

BACKGROUND OF THE INVENTION

The present invention comprises a new and distinct variety of *Dasiphora*, hereinafter referred to by the cultivar name 'MINPOROUG01'. This new *Dasiphora* was developed through a breeding program by the inventor at a nursery in La Menitre, France, by open pollination of the unpatented seed parent, *Dasiphora fruiticosa* 'Minora06'. The pollen parent is unknown. The objective of the breeding program was to develop new *Dasiphora* with reddish-orange flower color that is resistant to fading. The open pollination date resulting in the new variety was performed in July 2015.

The new variety was found and selected in September 2018. The first asexual propagation of 'MINPOROUG01' was carried out in September 2018 by softwood cuttings at the same nursery in La Menitre, France. 'MINPOROUG01' has been found to retain its distinctive characteristics through successive asexual propagations. Multiple generations have been propagated, with the new variety characteristics reproduced true to type.

Date of the first disclosure was Jun. 27, 2023, occurring in Grand Haven, Michigan. This disclosure was made directly by the inventor or one who obtained the claimed invention directly or indirectly from the inventor. This and all public disclosures made between Jun. 27, 2023 and the filing of this application fall within the exception allowed under 102(b)(1).

SUMMARY OF THE INVENTION

The following traits have been repeatedly observed and are determined to be the unique characteristics of *Dasiphora* 'MINPOROUG01'. These characteristics in combination distinguish 'MINPOROUG01' as a new and distinct *Dasiphora* cultivar:

1. Reddish-orange petal color with a pinkish-orange tint.
2. Fade-resistant flower color.
3. Densely-branched growth habit.
4. Easy propagation via softwood cuttings.

PARENT COMPARISON

'MINPOROUG01' is similar to the seed parent in most horticultural characteristics. 'MINPOROUG01' however differs in the following:

1. Flower color of the new variety is reddish-orange with a pinkish-orange tint, while the flower color of the seed parent is orange.
2. Plants of new variety are less vigorous than plants of the seed parent.

COMMERCIAL COMPARISON

'MINPOROUG01' is similar to the commercial variety *Potentilla fruticosa* 'JEFMAN', U.S. Plant Pat. No. 29,830, in most horticultural characteristics. 'MINPOROUG01' however differs in the following:

1. Fully-opened flower color of the new variety is reddish-orange, while the fully-opened flower color of this comparator is strictly orange.
2. Flower color of new variety is more resistant to fading than the flower color of this comparator.

BRIEF DESCRIPTION OF THE PHOTOGRAPHS

This new *Dasiphora* is illustrated by the accompanying photographs which show the plant's form, foliage and inflorescences. The colors shown are as true as can be reasonably obtained by conventional photographic procedures. Plants were grown in Grand Haven, Michigan.

FIG. 1. Shows a flowering plant of 'MINPOROUG01' in the ground at approximately 2 years old during Summer.

Figure 2:
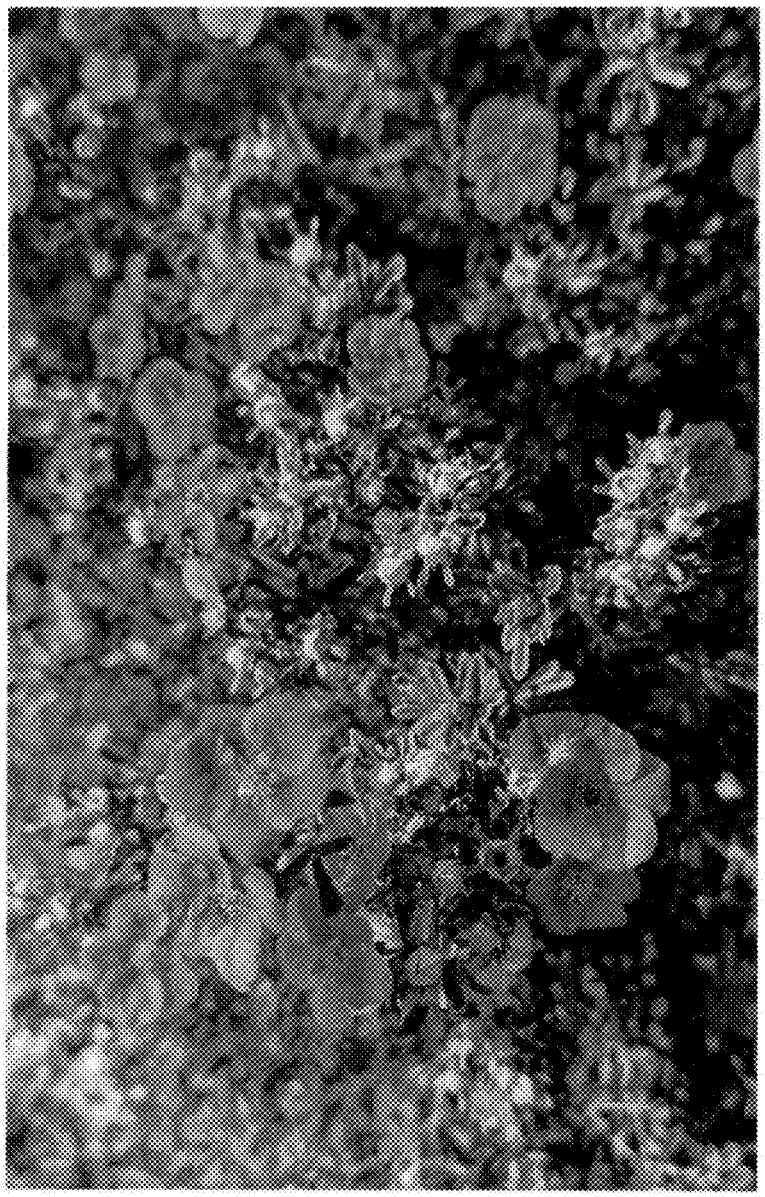

FIG. 2. Shows a close-up view of the flowers.

DETAILED BOTANICAL DESCRIPTION

In the following description, color references are made to The Royal Horticultural Society Colour Chart 2015 except where general terms of ordinary dictionary significance are used. The following observations and measurements describe 'MINPOROUG01' plants grown in a poly-greenhouse in Grand Haven, Michigan. The growing temperature ranged from 18° C. to 27° C. during the day and from 5° C. to 10° C. during the night. General light conditions are natural sunlight. Measurements and numerical values represent averages of typical plant types.

Botanical classification: *Dasiphora fruticosa* 'MINPOROUG01'.

PROPAGATION

Typical method: Softwood cuttings.

Time to initiate rooting: 5 to 7 days in summer at approximately 18° C. to 27° C.

Time to produce a rooted young plant: 3 weeks in summer at approximately 18° C. to 27° C.

Root description: Moderately dense, moderate branching, medium thickness, fibrous, and fleshy. Tan in color, not accurately measured with an RHS chart.

PLANT

Plant type: Perennial shrub.
Age of plant described: 2 to 3 years old.
Plant shape: Low mounded.
Growth habit: Upwards and outwards.
Height: 30 cm.
Plant spread: 44 cm.
Growth rate: Good.
Plant vigor: Fairly vigorous.
Branching characteristics: Basal, some pinching required.
Length of lateral branches: 22 cm.
Diameter of lateral branches: 3 mm.
Quantity of lateral branches: About 30.
Internode length: 1 cm.
Stem:
- *Shape.*—Rounded.
- *Aspect.*—10° to 60°.
- *Strength.*—Good.
- *Color.*—New growth: RHS Yellow-Green 145B. Old Growth: RHS Greyed-Orange 165A to 166A.
- *Pubescence.*—Slight, on new growth only.

FOLIAGE

Leaf:
- *Arrangement.*—Alternate, palmately compound.
- *Quantity of leaflets.*—5 to 7 per leaf.
- *Shape.*—Olanceolate to oblong.
- *Whole leaf length.*—1.5 cm.
- *Whole leaf width.*—2.5 cm.
- *Texture.*—Upper side: Soft, velvety, slightly pubescent. Under side: Soft, velvety, slightly pubescent.
- *Apex.*—Acute to obtuse.
- *Base.*—Cuneate.
- *Margin.*—Entire.
- *Color.*—Young, Upper side: Near RHS Yellow-Green 147B. Young, Under side: RHS Green 138B. Mature, Upper side: RHS Green 138B. Mature, Under side: RHS Green 138B.
- *Venation.*—Type: Palmate. Color: Upper side: RHS Yellow-Green 145B. Under side: RHS Yellow-Green 145B.

Petiole:
- *Length.*—3 mm.
- *Width.*—1 mm.
- *Texture.*—Upper side: Pubescent. Under side: Pubescent.
- *Color.*—Upper side: RHS Yellow-Green 145B. Under side: RHS Yellow-Green 145B.

FLOWER

Natural flowering season: Late spring to frost.
Inflorescence and flower type and habit: Single, rotate flowers, freely flowering from terminal ends of lateral branches.
Flowers per lateral stem: 2 to 6.
Buds per lateral stem: 2 to 6.
Flowers and buds per plant: 100 to 200.
Individual flower:
- *Type/form.*—Single rotate.
- *Shape.*—Single whorl.
- *Habit.*—Terminally.
- *Persistence.*—Self-cleaning.
- *Fragrance.*—None.
- *Aspect.*—Upwards and outwards.
- *Length.*—2.5 cm.
- *Diameter.*—2.5 cm.
- *Depth.*—3 mm.

Bud:
- *Shape.*—Ovate.
- *Length.*—7 mm.
- *Diameter.*—7 mm.
- *Color.*—RHS Yellow-Green 144C.

Petals:
- *Quantity.*—5.
- *Arrangement.*—Whorl, stellate.
- *Length.*—13 mm.
- *Width.*—12 mm.
- *Shape.*—Globose, orbicular.
- *Apex.*—Obtuse.
- *Base.*—Obtuse.
- *Margin.*—Entire, with slightly ruffled quality.
- *Texture.*—Upper side: Very soft and silky; glabrous. Under side: Very soft and silky; glabrous.
- *Color.*—When Opening, Upper Surface: RHS Orange-Red 34A to 34B. When Opening, Lower Surface: RHS Yellow 4C. Fully Opened, Upper Surface: RHS Orange-Red 31A. Fully Opened, Lower Surface: RHS Yellow 4C.

Sepals:
- *Arrangement.*—Whorl; stellate.
- *Appearance.*—Triangular shaped sepals with one leaf-like "spur" in between each.
- *Quantity.*—5 with 5 "spurs".
- *Length.*—6 mm.
- *Width.*—3 mm.
- *Shape.*—Widely triangular.
- *Margin.*—Entire.
- *Apex.*—Acute.
- *Base.*—Fused.
- *Color.*—Upper Side: RHS Yellow-Green 144C. Under Side: RHS Yellow-Green 144C.

*Texture.*—Upper side: Lightly pubescent. Lower side: Lightly pubescent.

Calyx:

*Shape.*—Collar-like.

*Length.*—1 cm.

*Diameter.*—1 cm.

Peduncle:

*Length.*—1 cm.

*Diameter.*—1 mm.

*Angle.*—45° relative to lateral branch.

*Strength.*—Good, somewhat flexible.

*Texture.*—Pubescent.

*Color.*—RHS Yellow-Green 144D.

REPRODUCTIVE ORGANS

Stamens:

*Number.*—About 20.

*Filament length.*—1 mm.

*Filament color.*—RHS Yellow 9B.

Anthers:

*Shape.*—Ovate.

*Length.*—0.5 mm.

*Color.*—RHS Greyed-Yellow 162A with Greyed-Orange 163A.

*Pollen amount.*—Scarce.

Pistil:

*Number.*—About 30.

*Length.*—Less than 0.5 mm.

*Style.*—Length: Less than 0.5 mm. Color: RHS Yellow 7A, fading to Green-White 157A at base.

*Stigma.*—Shape: Rounded. Color: RHS Yellow 7A.

OTHER CHARACTERISTICS

Fruit: Not observed to date.

Disease and insect resistance: No significant disease or pest resistance nor susceptibility have been observed.

Temperature range: Observed to tolerate temperatures between −31° C. and 38° C.

What is claimed is:

1. A new and distinct cultivar of *Dasiphora* plant named 'MINPOROUG01' as illustrated and described herein.

* * * * *